US006379721B1

(12) United States Patent
Sengupta et al.

(10) Patent No.: US 6,379,721 B1
(45) Date of Patent: Apr. 30, 2002

(54) **PROCESS FOR PREPARATION OF α-AMYLASE FROM *TINOSPORA CORDIFOLIA MIERS* USEFUL FOR STARCH SACCHARIFICATION**

(75) Inventors: Subhabrata Sengupta; Amal Kumar Naskar; Mohanlal Jana; Panchanan Naskar, all of Calcutta (IN)

(73) Assignee: Council for Scientific and Industrial Research (IN)

( * ) Notice: Subject to any disclaimer, the term of this patent is extended or adjusted under 35 U.S.C. 154(b) by 0 days.

(21) Appl. No.: 09/783,140

(22) Filed: Feb. 15, 2001

(51) Int. Cl.⁷ .................... A61K 35/78; A01N 65/00
(52) U.S. Cl. .................... 424/779; 424/725; 435/204
(58) Field of Search .................... 435/204; 424/725, 424/779

(56) References Cited

PUBLICATIONS

Web Site www.thehimalayadrugco.com/guduchi.htm "Himalaya Singles" *Tinospora cordifolia Miers* Sep. 12, 2001.*
Web Site www.thehimalayadrugco.com/h-tinosp.htm Sep. 12, 2001.*
Web Site www.gorkhaexim.com/products/herbtea/gurjop.htm.*

* cited by examiner

*Primary Examiner*—Herbert J. Lilling
(74) *Attorney, Agent, or Firm*—Dinesh Agarwal, P.C.

(57) ABSTRACT

The present invention provides a process for the preparation of α-amylase useful for starch saccharification from a novel plant source *Tinospora cordifolia* Miers belonging to Menispermaceae group of plant.

23 Claims, No Drawings

PROCESS FOR PREPARATION OF α-AMYLASE FROM *TINOSPORA CORDIFOLIA MIERS* USEFUL FOR STARCH SACCHARIFICATION

FIELD OF THE INVENTION

The present invention relates to a process for the preparation of α-amylase, useful for starch saccharification from a novel plant source *Tinospora cordifolia* Miers belonging to Menispermaceae group of plants. The present invention particularly relates to a process for the preparation of a novel α-amylase, which saccharify starch mainly into maltose and glucose.

BACKGROUND OF THE INVENTION AND PRIOR ART DISCUSSION

Starch degrading α-amylase enzyme have large numbers of biotechnological applications e.g. in the productions of syrups containing oligosaccharides, maltose and glucose from corn and other starchy materials, fermentable carbohydrate for ethanol production by saccharification of corn or other starchy materials and as digestive enzyme in pharmaceutical preparations, as thinning agent in lowering viscosity of commercial starch preparations, improving enzyme in bread making and in many other applications. The traditional process of acid catalyzed saccharification of starch into syrup or fermentable sugars has largely been replaced for many advantageous reasons by the enzymatic processes using α-amylase. References may be made to H. C. Barford, Cereal Foods World 21, 588, 1976 and L. A. Underkofler, L. J. Denault and E. F. Hon, Die Starke 17, 179, 1965.

The enzyme α-amylase (α-1,4 D-glucan glucanohydrolase Enzyme commission number 3.2.1.1) is widely produced by different microorganisms and is also present in some cereals. It hydrolyses α-1,4-glucosidic linkages present in amylose, amylopectin and glycogen in an endo-fashion. But it does not hydrolyze α-1,6-glucosidic branch point present in amylopectin. Saccharification of amylose and amylopectin by α-amylase produces, maltose, maltotriose and glucose and a series of branched α-limit dextrins respectively. The amount and nature of α-limit dextrins varied with the nature of α-amylase obtained from different sources.

The enzyme produced by microorganism may be saccharifying or liquefying in nature. Saccharifying enzyme produces more reducing sugar from starch than the liquefying enzyme, but later lower viscosity of starch more quickly than the former enzyme. *Bacillus subtilis* var *amylosaccharficus, Bacillus subtilis* Marburg, *Bacillus subtilis* Natto are potential producers of saccharifying α-amylase. Reference may be made to H. Matsuzaki, K. Tamane, K. Yamaguchi, Y. Naguta and B. Maru Biochimica Biophysica Acta 365, 235, 1974. *Bacillus amyloliqurefaciens* produces large amount of liquefying α-amylase. Reference may be made to N. G. Welkar and L. L. Campbell. Journal of Bacteriology 94, 1131, 1967, Saccharifying α-amylase is immunologically different from liquefying enzyme and in having maltase activity. Reference may be made to H. Yoshida, K. Hiromi and S. Ono. Journal of Biochemistry, Tokyo, 62, 439, 1967. Saccharifying α-amylase has tremendous uses in the production of syrup and fermentable carbohydrate from starchy raw materials and in medicine. Grain starch as carbon source, is used to the extent of 50% of total substrate for ethanol production. Liquefying amylase is used for quickly reducing viscosity of starch solution. Germinating cereals also contain saccharifying α-amylase. Traditional starch hydrolysis is usually conducted using barley malt. Malt is obtained mainly from barley, sometimes also from wheat and oats. The cereals are allowed to germinate for a limited period of time and then dried under suitable condition to terminate growth of embryo. The ground powder of the dried cereals is used as the source of enzyme. In beer preparation, malt is used both as source of enzyme and source of carbohydrate for fermentation. In the preparation of whisky and other liquors, gelatinized starch is saccharified by malt enzyme and the hydrolysed product is fermented.

As an alternative to barley malt, saccharifying α-amylase produced by different fungi are also largely used. Mold bran containing growth of *Aspergillus oryzae* is traditionally used for starch hydrolysis. Reference may be made to J. Ziffer and M. C. Losit. Biotechnology Letters 4, 573, 1982. Submerged fermentation process for the production of saccharifying α-amylase was also developed and enzymes from *Mucor touxii, Mucor boulard, Rizopus delemer* etc. were used for starch saccharification.

However, the production of saccharifying α-amylase by malting barley is a highly technical exercise, which depends on the use of selected varieties of cereals and on the malting technique, which was developed as an art over hundreds of year. On the other hand, bacterial and fungal enzymes have restricted use in food preparations. In the industrial production of fungal enzyme, frequent allergic outbreaks were reported time to time, possibly due to spreading of fungal spores in the environment.

OBJECTS OF THE INVENTION

The main object of the present invention is to provide a process for the preparation of α-amylase useful for starch saccharification from a novel plant source *Tinospora cordifolia* Miers belonging to Menispermaceae group of plant.

Another object of the present invention is to provide a process for the preparation of α-amylase wherein the enzyme preparation does not require presence of calcium ion for optimum activity.

Still another object of the present invention is to provide a process for the preparation of α-amylase wherein the saccharifying enzyme has α-glucosidase activity which hydrolyses maltose.

Yet another object of the present invention is to provide a process for the preparation of α-amylase wherein the production of enzyme does not require any controlled environmental conditions like malting or growth of microorganism under defined physicochemical conditions.

One more object of the present invention is to provide a process for the preparation of α-amylase wherein the crude enzyme preparation contains mostly α-amylase protein with little non-amylase contaminating protein.

One another object of the present invention is to provide a process for the preparation of α-amylase wherein the enzyme preparation become homogeneous protein in gel electrophoresis in presence of sodium dodecyl sulphate by a single step process involving ion exchange chromatography.

Another object of the present invention is to provide a process for the preparation of α-amylase wherein the enzyme preparation under suitable conditions could digest soluble starch until the degree of polymerization is between 2 and 3.

Still another object of the present invention is to provide a process for the preparation of α-amylase wherein the enzyme preparation under suitable conditions could digest soluble starch to generate up to 20% free glucose.

Yet another object of the present invention is to provide a process for the preparation of α-amylase wherein the starting material used as the source enzyme is a plant which has been known to be edible to humans for a longtime.

One more object of the present invention is to provide a process for the preparation of α-amylase wherein the plant used as starting material is not a vegetable or fodder having alternative demand.

One another object of the present invention is to provide a process for the preparation of α-amylase wherein the plant used as starting material grows wild throughout the whole seasons.

Another object of the present invention is to provide a process for the preparation of α-amylase wherein the plant used as starting material could grow from any part of the mature stem under proper growth supporting environments.

SUMMARY OF THE INVENTION

The present invention provides a process for the preparation of α-amylase useful for starch saccharification from a novel plant source *Tinospora cordifolia* Miers belonging to Menispermaceae group of plant.

DETAILED DESCRIPTION OF THE INVENTION

Accordingly, the present invention provides a process for the preparation of α-amylase useful for starch saccharification, which includes blending cut pieces of *Tinospora codifolia* Miers stem in an aqueous medium at a pH of 4.5 to 8.0 and a temperature between 0°–50° C., separating the aqueous phase by a known process of filtration, concentrating the extract by a known process of enzyme concentration, isolating the pure α-amylase by conventional protein purification methods.

In an embodiment of the present invention, the extraction medium used is water, acidulated water or mild alkaline water of pH from 4.5 to 8.0, buffer of pH 4.5 to 8.0, or water containing 0–10% (v/v) organic solvents such as acetone or ethanol.

In a preferred embodiment of the present invention, the pH value of the medium is between 5 and 6.

In another preferred embodiment of the present invention, the temperature of the liquid medium is maintained at 30° C.

In another embodiment of the present invention, the reagents used for the precipitation of enzyme are selected from the group consisting of acetone, ethanol, polyethylene glycol, ammonium sulphate, and sodium sulphate.

In still another embodiment of the present invention, process used for the concentration of enzyme solution is selected from the group comprising of ultrafiltration, lypophilisation, vacuum distillation and aqueous two-phase systems containing dextran or sodium chloride etc.

In yet another embodiment of the present invention, purification of α-amylase is done by ion exchangers or gel filtration method.

In another embodiment of the present invention, the ion exchangers used for the purification of α-amylase are weak anion exchangers or weak cation exchangers.

In still another embodiment of the present invention, weak anion exchangers used for the purification of α-amylase are one or more of diethylaminoethyl (DEAE)-sephadex, DEAE-cellulose, DEAE-sepharose, DEAE-sephacel, DEAE-cellulose, Epichlorohydrin triethanolamine-cellulose, Diethyl-[2-hydroxypropylamino ethyl (QAE)]-Sephadex, QAE-cellulose and DEAE-Trisamyl.

In yet another embodiment of the present invention, cation exchangers used for the purification of α-amylase are one or more of carboxymethyl (CM)-Sephadex, CM-agarose, CM-cellulose, Sulfopropyl- (SP)-Sephadex, SP-sepharose and Cellulose phosphate sulfoxyethyl-cellulose.

In one more embodiment of the present invention, gel filter media used for the purification of α-amylase are one or more of sephadex, sephacryl, sepharose, superose, tyopearls, ultrogel and beaded cellulose.

In one another embodiment of the present invention, production of enzymes does not require any controlled environmental conditions such as malting or growth of microorganism under defined physiochemical conditions.

In another embodiment of the present invention, production of enzymes does not require presence of calcium ion.

In still another embodiment of the present invention, the crude enzyme contains mostly α-amylase protein with little non-amylase contaminating protein.

In yet another embodiment of the present invention, the enzyme preparation become homogeneous protein gel electrophoresis in the presence of sodium dodecyl sulphate by a single step process involving ion exchange chromatography.

In one more embodiment of the present invention, the enzyme prepared could digest soluble starch until the degree of polymerization is between 2 and 3.

In another embodiment of the present invention, the enzyme prepared could digest soluble starch to generate up to 20% free gluose.

In another embodiment of the present invention, the extract may be used as a direct source of saccharifying α-amylase.

In still another embodiment of the present invention, the enzyme has highest activity between temperatures of 60° and 65° C. and at a pH of 6.0±0.2.

In yet another embodiment of the present invention, the activity was found to be stable up to a temperature of 60° C. and a pH of 7.5.

In another embodiment of the present invention, total recovery of α-amylase activity was about 980 units.

In one another embodiment of the present invention, the enzyme gave a single protein band of 43-kilodalton weight in SDS-PAGE.

In another embodiment of the present invention, total recovery of α-amylase activity was 980 units.

The enzyme is obtained from the plant *Tinospora cordifolia* Miers, is a known medicinal plant called by different names like Guruchi, Amritballi, Gulancha, Tippatigi, Sindi, Guthabael, Golo etc in different regions of India and abroad. It grows throughout the tropical India, Maynamar, and Srilanka. Reference may be made to Indian Medicinal plants, Volume 1, Edited by Lt.Col. K. R Kirtikar, Major B D Basu and An I.C.S, Revised by E Blatter, J. F Caius and K s Mhaskar, pp 77–80 Published by Bishen Sing Mahendra Pal Sing, Cannught Place, Dehradunn-248001, India (1998).

The mature plants grown wild in different fields were collected and sorted to eliminate infected part, if any. Stem parts having a thickness of more than 2 millimeters were freed from leaves and thoroughly washed with water. These stems were cut into thin slices of 1–3 mm thickness by sharp knife. The cut pieces were immersed immediately in water or a buffer of pH from 4.5 to 8.0, preferably of pH 5.0 to 6.0. Volume of liquid was from 100 ml to 500 ml per 100 gram of green stem, preferably 200 ml per 100-gram plant.

Temperature of the extracting liquid was 0–50° C., preferably below 30° C. The mixture was blended in a Waring blender to obtain a paste of the biomass. The mass was squeezed through a nylon cloth to obtain a greenish liquid free from cellulosic fiber. The residue was resuspended in the same volume of water and re-blended for 1 minute and similarly passed through nylon cloth. The total filtered liquid was kept for 4 hours at room temperature when precipitation of a white mass takes place. The clear liquid was filtered out under suction. The clear liquid could be used as the source of saccharifying α-amylase enzyme, which contains α-amylase, as the major constituent protein along with some minor proteins in the solution. The saccharifying enzyme was purified either by gel filtration medium capable of separating proteins of molecular weight between 40–50 kilodalton, or by absorption of weak amino exchanger, preferably DEAE-cellulose at pH 5–6.0 and elution under 0–1M salt gradient or by passing through a weak cation exchanger, preferably CM-cellulose and collecting the extract. The enzyme purified by any one of the process is a homogeneous protein as found by sodium dedecyl sulphate-polyacrylamide gel electrophoresis. The molecular weight is in the range of 40–45 kilodalton.

The enzyme activity is determined by estimating the amount of reducing sugar liberated from the substrate by dinitrosalicylic acid method. Reference may be made to J. B. Sumner and G. Sumner in "Laboratory Experiments in Chemistry" Academic Press, New York, pp.38, 1949. Unit of enzyme activity was taken as the amount of enzyme, which could liberate one micromole of maltose equivalent per minute in buffer of pH 6.0 at 50° C. The α-glucosidase activity of the enzyme preparation before purification was assayed with p-nitrophenyl-α-D-glucoside as substrate. Reference may be made to S. Sengupta and S. Sengupta. Canadian Journal of Microbiology 36 (9), 617, 1990. One unit of enzyme activity was taken as the amount of enzyme which could liberate one micromole of p-nitrophenol from p-nitrophenyl-α-D-glucoside in the reaction mixture incubated at 50° C. for 30 minutes. The α-amylase activity of the purified or of the unpurified extract active on starch in the pH range of 4 to 7.5, optimally at 6.0, at temperature between 20–70° C., optimally at 60° C., with velocity maximum (Vm) value on Michaelis constant (Km) value being 34.8 unit per milligram of protein and 3.75 mg soluble potato starch per milliliter in the incubation mixture. The enzyme activity does not require any calcium ion for optimum activity. The enzyme, under optimum reaction condition, for example pH temperature, enzyme-substrate ratio (Km) digest soluble potato starch to reducing sugar of degree of polymerization between 2–3. The micelles constant (Km) value of enzyme with soluble potato starch as substrate varies from 3.5–4.0 mg soluble starch/milliliter and the corresponding velocity maximum value ranged from 30–40 μmoles of reducing group per minute per milligram of protein at the incubation temperature of 50° C.

The following examples are provided as illustration of the present invention and should not be construed to limit the scope of the present invention.

EXAMPLE-1

The stem of the plant *Tinospora codifolia* Miers, grown wild were collected and sorted to remove leaves and stems of diameter less than 2 millimeter were discarded. The stems free from any superficial infection were washed and cut into small pieces of 0.5 to 1 centimeter long. Biomass of 108 gram wet weight was mixed with 200 ml of water at 20° C. and blended for 3 minutes in a Waring blender. A nylon cloth squeezed the blended mass and 175 ml of extract was obtained. The extract had 8,000 unit of enzyme activity. The biomass left was further blended with 200 ml of water and filtered by the way as done earlier. 190 ml of extract was obtained containing 2,450 units of enzyme. The whole mass was mixed and kept at room temperature when a precipitate was formed. The precipitate was removed by the vacuum filtration and 350 ml of clear extract containing 10,200 units of enzyme was obtained. The extract may be used directly as the source of saccharifying α-amylase. The enzyme had highest activity between temperature 60° C.±5 and at pH 6.0±0.2. The activity was stable up to 60° C. and pH 7.5 The enzyme hydrolyzed 30% (w/v) gelatinized soluble starch 500 unit per gm of starch at 60° C., to the degree of polymerization of 2.8 with 30% glucose with respect to the amount reducing group liberated. The enzyme was purified further from the extract by passing through a DEAE cellulose column equilibrated at pH 5.0. The activity adsorbed on to the column was eluted by 0–1 M sodium chloride gradient. The enzyme eluted from the column was concentrated by lyophisation or by ultrafiltration. Recovery of the purified enzyme was 30% of the total charged. The preparation gave a single protein band between 40–45 killodalton in sodium dodecyl sulphate polyacrylamide (SDS-PAGE) gel electrophoresis.

EXAMPLE-2

The wild plants were collected, sorted to remove leaves and thin stem of diameter less than 2 mm. Any infected stems observed were discarded. The plants (200 gm wet weight) were washed with cold water, dried over cloth and stored at temperature between 20–30° C. for one month under dry condition. The dried mass was cut into small pieces by scissors and suspended in 400 ml of 0.1M acetate buffer, pH 5.0. The whole was kept for one hour at room temperature (25° C.) and then blended for 4 minutes in a Waring blender. The blended mass was filtered over filter paper in vacuum filter and filtrate was collected. The biomass remaining was further suspended in 400 ml 0.1M acetate buffer, pH 5.0 and blended and filtered by vacuum filtration. The total supernatant 720 ml contained 16,850 units of α-amylase and 1,674 units of α-glucosidase enzyme. The crude extract may be used directly as the source of saccarifying α-amylase. The activity of the enzyme on soluble starch was highest at 60±0.01. The enzyme hydrolyzes 25% starch at 60° C. to the degree of polymerization of 2.5 with 25% glucose with respect to the amount of reducing group liberated. Amount of enzyme used was 400 unit/gm of soluble starch. The enzyme was purified by passing through a CM-cellulose column equilibrated at pH 5.0. The activity passed through the column was found to be homogeneous to give a single band of molecular weight between 40–45 kilo dalton in SDS-PAGE.

EXAMPLE-3

The wild plants are collected fresh and sorted to remove leaves and infected stem. The stems are then washed with cold water, dried over cloth and weighed. The mass (100-gram) was sliced by a sharp knife (0.2–0.5 millimeter) thickness and immersed in 300 ml of water. The mixture was kept in a refrigerator overnight. The extract (190 ml) was removed and it contained 7,240 unit of enzyme. The biomass was further mixed with 200 ml of water and blended in a Waring blender for 4 minutes. The mixture was filtered over a filter paper on vacuum filter and extract (185 ml) was collected. The extract contained 3,800 units of α-amylase.

The total extract (375-ml) had 930 units of α-glucosidase activity. The extract may be used directly as the source of saccharifying α-amylase. The enzyme was optimally active at pH 6.0±0.2 and temperature 60±4° C. on soluble starch and was stable up to 60° C. and pH 7.5.

The enzyme from the extract was precipitated by ammonium sulphate when it was precipitated with a gum. The enzyme was extracted with water when it solubulizes, but the precipitate did not. The recovery of enzyme was 2,400 units only. A gel filtration column BIOGEL P-60 using 0.1M sodium acetate buffer, pH 5.0 as the eluant, purified the concentrated protein solution. The enzyme eluted as a major protein peak from the column was found to be pure. It gave a single protein band of molecular weight between 40–45 kilo dalton in SDS-PAGE. Total recovery of α-amylase activity was 980 units. The enzyme was optimally active on soluble starch at temperature of 60±1° C., pH 6.0±0.1 and was stable up to 60±3° C. and pH 7.5.

The Main Advantage of the Process of the Present Invention are

1. The saccharifying amylase preparation is obtained from an edible plant source *Tinospora cordifolia* Miers.
2. The α-amylase is a saccharifying α-amylase suitable for saccharification of starch mainly into maltose and glucose.
3. The α-glucosidase activity was also present with α-amylase, which allows production of glucose from maltose.
4. The plant to be used as the source of enzyme is not a food or fodder.
5. The α-amylase represents the major protein present in the extract of the plant and thus requires only single step for purification.
6. No process technology like malting or fermentation process is required for the production of enzyme.
7. The source of plant is a wild one and does not require special agro-conditions for growth.
8. The enzyme does not require any ions like calcium for activation.
9. The activity of the enzyme is stable within the dry plant kept under dry environment at room temperature up to 3 to 4 months.
10. The enzyme has temperature optimum at 60° C. which is higher than those *Aspergillus oryzae, Aspergillus niger* and malt diastase which are used for starch syrup preparation.
11. The enzyme is optimally active near neutral (pH 6.0) condition and does not require addition of acid or alkali to the reaction mixture for adjustment of pH.
12. The enzyme is present in the plant extract in a more purified state compared to malt or microbial enzymes.
13. The enzyme could be purified more easily than malt or microbial enzyme.

What is claimed is:

1. A process for the preparation of α-amylase, useful for starch saccharification, said process comprising:
    blending cut pieces of *Tinospora codifolia* Miers stem in a liquid medium at a pH of 4.5 to 8.0 between 0–50° C.,
    separating the aqueous phase by filtration,
    concentrating the extract by enzyme concentration, and
    isolating the pure α-amylase by protein purification.

2. A process as claimed in claim 1, wherein the liquid medium is selected from the group consisting of water, acidulated water or mild alkaline water of pH from 4.5 to 8.0, buffer of pH 4.5 to 8.0, and water containing 0–10% (v/v) acetone or ethanol as an organic solvent.

3. A process as claimed in claim 1, wherein the pH of the liquid medium is between 5 and 6.

4. A process as claimed in claim 1, wherein the temperature of the liquid medium is maintained at 30° C.

5. A process as claimed in claim 1, wherein the reagents used for the precipitation of enzyme are selected from the group consisting of acetone, ethanol, polyethylene glycol, ammonium sulphate, and sodium sulphate.

6. A process as claimed in claim 1, wherein the process for the concentration of enzyme solution is selected from the group consisting of lyophilisation, ultrafiltration, vacuum distillation, salt precipitation, and solvent precipitation of protein.

7. A process as claimed in claim 1, wherein the purification of α-amylase is done by ion exchangers or gel filtration.

8. A process as claimed in claim 1, wherein the ion exchangers used for the purification of α-amylase are selected from the group consisting of weak anion exchangers, and weak cation exchangers.

9. A process as claimed in claim 1, wherein the weak anion exchangers used for the purification of α-amylase are selected from the group consisting of diethylaminoethyl (DEAE)-sephadex, DEAE-cellulose, DEAE-sepharose, DEAE-sephacel, DEAE-cellulose, Epichlorohydrin triethanolamine-cellulose, Diethyl-[2-hydroxypropylamino ethyl (QAE)]-Sephadex, QAE-cellulose, and DEAE-Trisamyl.

10. A process as claimed in claim 1, wherein the cation exchangers used for the purification of α-amylase are selected from the group consisting of carboxymethyl (CM)-Sephadex, CM-agarose, CM-cellulose, Sulfopropyl-(SP)-Sephadex, SP-sepharose, and Cellulose phosphate sulfoxyethyl-cellulose.

11. A process as claimed in claim 1, wherein the gel filter medium used for the purification of α-amylase is selected from the group consisting of BioGel, sephadex, sephacryl, sepharose, superose, tyopearls, ultrogel, and beaded cellulose.

12. A process as claimed in claim 1, wherein the production of enzymes does not require malting or growth of microorganism under physiochemical conditions.

13. A process as claimed in claim 1, wherein the production of enzymes does not require presence of calcium ion.

14. A process as claimed in claim 1, wherein the crude enzyme comprises α-amylase protein with non-amylase contaminating protein.

15. A process as claimed in claim 1, wherein the enzyme preparation becomes homogeneous protein in gel electrophoresis in the presence of sodium dodecyl sulphate by a singe step process involving ion exchange chromatography.

16. A process as claimed in claim 1, wherein the enzyme prepared could digest soluble starch until degree of polymerization is between 2 and 3.

17. A process as claimed in claim 1, wherein the enzyme prepared could digest soluble starch to generate up to 20% free glucose.

18. A process as claimed in claim 1, wherein the extract comprises a direct source of saccharifying α-amylase.

19. A process as claimed in claim 1, wherein the enzyme has a highest activity between temperatures of 60° and 65° C. and at a pH of 6.0±0.2.

20. A process as claimed in claim 1, wherein the activity is stable upto 60° C. and pH 7.5.

21. A process as claimed in claim 1, wherein the extract comprises 3,800 units of α-amylase.

22. A process as claimed in claim 1, wherein the enzyme comprises a single protein band of 43-kilodalton weight in SDS-PAGE.

23. A process as claimed in claim 1, wherein the total recovery of α-amylase activity comprises 980 units.

* * * * *